US011232293B2

(12) United States Patent
Momcilovic et al.

(10) Patent No.: US 11,232,293 B2
(45) Date of Patent: *Jan. 25, 2022

(54) ACTIVE MARKER DEVICE FOR PERFORMANCE CAPTURE

(71) Applicant: Weta Digital Limited, Wllington (NZ)

(72) Inventors: Dejan Momcilovic, Wellington (NZ); Jake Botting, Wellington (NZ)

(73) Assignee: WETA DIGITAL LIMITED, Wellington (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/332,729

(22) Filed: May 27, 2021

(65) Prior Publication Data

US 2021/0295026 A1    Sep. 23, 2021

Related U.S. Application Data

(63) Continuation of application No. 17/163,267, filed on Jan. 29, 2021, now Pat. No. 11,048,925.

(60) Provisional application No. 63/072,081, filed on Aug. 28, 2020, provisional application No. 63/072,082, filed on Aug. 28, 2020, provisional application No. 62/983,523, filed on Feb. 28, 2020.

(51) Int. Cl.
*G06K 9/00* (2006.01)
*G06T 7/593* (2017.01)
*G06T 7/20* (2017.01)

(52) U.S. Cl.
CPC ........... *G06K 9/00342* (2013.01); *G06T 7/20* (2013.01); *G06T 7/593* (2017.01); *G06T 2207/30196* (2013.01); *G06T 2207/30208* (2013.01)

(58) Field of Classification Search
None
See application file for complete search history.

(56) References Cited

U.S. PATENT DOCUMENTS 6,324,296 B1   11/2001   McSheery
6,801,637 B2   10/2004   Voronnka
(Continued)

FOREIGN PATENT DOCUMENTS

WO    2018054338 A1    3/2018

OTHER PUBLICATIONS

Chatzitofis et al., "DeepMoCap: deep optical motion capture using multiple depth sensors and retro-reflectors", 2019 (Year: 2019).
(Continued)

*Primary Examiner* — Soo Jin Park
(74) *Attorney, Agent, or Firm* — Trellis IP Law Group, PC; Lisa Benado

(57) ABSTRACT

A performance capture system is provided to detect one or more active marker units in a live action scene. Active marker units emanate at least one wavelength of light that is captured by the performance capture system and used to detect the active markers in the scene. The system detects the presence of the light as a light patch in a capture frames and determines if the light patch represents light from an active marker unit. In some implementations, various active markers in a scene may emanate different wavelengths of light. For example, wavelengths of light from multi-emitting active marker units may be changed due to various conditions in the scene.

20 Claims, 7 Drawing Sheets

(56) References Cited

U.S. PATENT DOCUMENTS

| | | | |
|---|---|---|---|
| 7,629,994 B2 * | 12/2009 | Dobrin | H04N 5/247 |
| | | | 348/139 |
| 10,373,517 B2 | 8/2019 | Becker | |
| 10,573,050 B1 * | 2/2020 | Liu | G06T 13/40 |
| 10,593,101 B1 * | 3/2020 | Han | G06F 3/011 |
| 10,657,704 B1 | 5/2020 | Han | |
| 10,701,253 B2 | 6/2020 | Knoll | |
| 10,812,693 B2 * | 10/2020 | Estebecorena | H04N 5/2253 |
| 2004/0161246 A1 | 8/2004 | Matsutshita | |
| 2005/0105772 A1 | 5/2005 | Voronka | |
| 2008/0246694 A1 | 10/2008 | Fischer | |
| 2009/0270193 A1 | 10/2009 | Stremmel | |
| 2011/0025853 A1 * | 2/2011 | Richardson | H04N 5/247 |
| | | | 348/159 |
| 2012/0307021 A1 | 12/2012 | Tsai | |
| 2014/0320667 A1 | 10/2014 | Densham | |
| 2015/0336012 A1 | 11/2015 | Stenzler | |
| 2015/0336013 A1 * | 11/2015 | Stenzler | G06K 9/00771 |
| | | | 700/90 |
| 2015/0356737 A1 | 12/2015 | Ellsworth | |
| 2017/0177939 A1 | 6/2017 | Beall | |
| 2017/0305331 A1 | 10/2017 | Soehner | |
| 2017/0366805 A1 | 12/2017 | Sevostjanov | |
| 2018/0131880 A1 | 5/2018 | Hicks | |
| 2018/0306898 A1 | 10/2018 | Pusch | |
| 2019/0257912 A1 | 8/2019 | Remelius | |

OTHER PUBLICATIONS

Nageli et al., "Flycn: real-time environment-independent multi-view human pose estimation with aerial vehicles", 2018 (Year: 2018).

* cited by examiner

ACTIVE MARKER DEVICE FOR PERFORMANCE CAPTURE

CROSS REFERENCES TO RELATED APPLICATIONS

This application is a continuation of U.S. patent application Ser. No. 17/163,267, entitled "Active Marker Device For Performance Capture," filed on Jan. 29, 2021 (WD0032US1) which claims priority from U.S. Provisional Patent Application No. 62/983,523, entitled "Active Marker Device For Performance Capture," filed on Feb. 28, 2020 (WD0032PP1); U.S. Provisional Patent Application No. 62/983,52, entitled "Active Marker Strobing For Performance Capture Communication," filed on Aug. 28, 2020 (WD0065PP1); and U.S. Provisional Patent Application No. 63/072,082, entitled "Strobing By Active Marker Groups In Performance Capture," filed on Aug. 28, 2020 (WD0065PP2), all of which are hereby incorporated by reference as if set forth in full in this application for all purposes.

FIELD OF THE INVENTION

The present disclosure generally relates to visual productions and more particularly to detecting active markers in a live action scene for performance capture systems.

BACKGROUND

Visual productions often combine real and digital images to create animation and special effects. Such visual productions can include movies, videos, clips, and recorded visual media. Performance capture (or "motion capture") systems may be employed to obtain information about an actor on a location shoot, such as the person's shape, movement, and facial expression. Light captured from markers on physical objects in a live scene is used to create a computer-generated ("CG," "virtual," or "digital") character. Light from the markers are recorded to establish position, orientation, and/or movement of the objects to which the markers are attached. Recording of live action can require many costly "takes" if a shot is not right.

The live action shoot may occur in various settings and under a variety of conditions. For example, light from the markers should be isolated from different types of interfering non-marker lights such as natural sunlight or miscellaneous reflections of light, on the set. The light from the markers needs to be detectable in diverse situations.

SUMMARY

A performance capture system associated with a visual production is provided to detect one or more active marker units coupled to one or more respective objects in a live action scene. At least one wavelength of light emanating from the active marker unit is captured by the performance capture system as a light patch in a frame. The captured light is determined to represent a particular active marker unit when it meets certain criteria. The criteria include that light patch is captured during a block of time that corresponds with a respective predefined frame of the scene produced by the performance capture system. Other criteria includes that the light patch meets one or more trigger thresholds in the predefined frame. In some implementations, various active marker units in a scene may emanate different wavelengths of light. For example, wavelengths of light from active marker units may be changed due to various conditions in the scene.

In some implementations, a method is provided that employs one or more active marker units attached to an object in a live action scene, and which are configured to emanate at least one wavelength of light in response to signals received from a signal controller. A plurality of sensor devices capture the presence of light from the live action scene. The presence of light is captured as a light patch in capture frames produced by the plurality of sensor devices. One or more processors generate marker data associated with the captured presence of light. The one or more processors determine that the light patch represents at least one of the one or more active marker units, based on the marker data meeting particular criteria. The criteria include that the capture frames correspond with predefined frames in a block of time expected to include the at least one wavelength of light emanating from the active marker units. The criteria also include that the light patch meets a trigger threshold. The trigger threshold including one or more of: a threshold size of the light patch, or an intensity threshold of the light patch compared to a pixel area proximal to the light patch. The criteria may also include verification that the light patch is captured by at least two sensor devices of the plurality of sensor devices during the block of time.

In some implementations, a first active marker unit may emanate a first wavelength of light and a second active marker unit may emanate a second wavelength of light that is different from the first wavelength of light. In these implementations, a first sensor device may capture the first wavelength of light and a second sensor device may capture the second wavelength of light.

In some implementations, at least one multi-emitting active marker unit may be configured to emanate a first wavelength of light at a first time period and emanate a second wavelength of light at a second time period. Target light parameters may be determined that are suitable for a current condition of the active marker units in the live action scene. A function of the at least one active marker unit may be adjusted according to the target light parameters, including changing the wavelength of light emanating from the at least one active marker unit. At least one multi-emitting active marker unit of the one or more active marker units may simultaneously emanate a first wavelength of light and a second wavelength of light. In some implementations, the method may also include adjusting of at least one parameter of sensor devices to fix on the light patch and generate more precise marker data. Adjustments may be made to aperture, contrast, focus, or exposure. The method may further include masking of the pixel area surrounding the light patch to exclude interfering light. Such adjustments and masking may facilitate assessment of the light patch to determine if the light patch represents light from an active marker unit, for example to determine a size of a light patch.

In some implications, a non-transitory computer-readable storage medium is provided that carries program instructions to detect one or more active marker units in attached to an object in a live action scene of a visual production. The active marker units are configured to emanate at least one wavelength of light in response to signals received from a signal controller. The program instructions, when executed by one or more processors, cause the one or more processors to perform operations. The operations may include generating marker data associated with a captured presence of light from a live action scene. The presence of light is captured as a light patch in capture frames produced by a plurality of sensor devices. The operations further may include determining that the light patch represents at least one of the one or more active marker units attached to an object in a live action scene. Each of the active marker units are configured to emanate at least one wavelength of light in response to signals received from a signal controller. The determination is based on the marker data meeting particular criteria. The criteria include that the capture frames correspond with predefined frames in a block of time expected to include the at least one wavelength of light emanating from the active marker units. The criteria also include that the light patch meets a trigger threshold including one or more of: a threshold size of the light patch, or an intensity threshold of the light patch compared to a pixel area proximal to the light patch. In some implementations, the criteria further may include a verification that the light patch may be captured by at least two sensor devices of the plurality of sensor devices during the block of time.

In some implementations, the marker data may include first marker data associated with a first wavelength of light emanating at a first time period from at least one active marker unit of the plurality of active marker units. The marker data may also include a second wavelength of light that is different from the first wavelength of light, emanating from the at least one active marker unit at a second time period. At times, the operations may further comprise determining target light parameters suitable for a current condition. The function of the at least one active marker unit may be adjusted according to the target light parameters, such as changing the wavelength of light emanating by the at least one active marker unit.

In some implementations, the marker data may be associated with a first wavelength of light and a second wavelength of light simultaneously emanating from a first active marker unit. At times, the operations may further comprise adjusting at least one parameter of the plurality of sensor devices to fix on the light patch, including adjusting one or more of: aperture, contrast, focus, or exposure; and masking the pixel area surrounding the light patch to exclude interfering light.

A system may be provided to detect an active marker unit in performance capture associated with a visual production. Such system includes one or more active marker units in attached to an object in a live action scene of a visual production. Each of the one or more active marker units may be configured to emanate at least one wavelength of light in response to signals received from a signal controller. The system also includes a plurality of sensor device of a performance capture system, configured to capture a presence of light from the live action scene. Such presence of light may be captured as a light patch in capture frames produced by the plurality of sensor devices. The system includes a computer device having one or more processors and one or more non-transitory computer-readable media with logic encoded thereon. The one or more processors execute the logic to perform operations. Such operations may include generating marker data associated with the captured presence of light; and determining that the light patch represents at least one of the one or more active marker units, based on the marker data meeting particular criteria. The criteria may include: the capture frames correspond with predefined frames in a block of time expected to include the at least one wavelength of light emanating from the active marker units. Further criteria may include that the light patch meets a trigger threshold including one or more of: a threshold size of the light patch, or an intensity threshold of the light patch compared to a pixel area proximal to the light patch. In some implementations, the criteria may also include verification that the light patch may be captured by at least two sensor devices of the plurality of sensor devices during the block of time.

In some implementations, the one or more active marker units may include a first active marker unit that emanates a first wavelength of light and a second active marker unit that emanates a second wavelength of light. The second wavelength of light is different from the first wavelength of light. In some implementations, at least one multi-emitting active marker unit of the one or more active marker units may be configured to emanate a first wavelength of light at a first time period and emanate a second wavelength of light at a second time period. In still some implementations, at least one multi-emitting active marker unit of the one or more active marker units simultaneously emanates a first wavelength of light and a second wavelength of light.

In some implementations, the operations of the one or more processors may further comprise adjusting at least one parameter of the plurality of sensor devices to fix on the light patch, including adjusting one or more of: aperture, contrast, focus, or exposure, and masking the pixel area surrounding the light patch to exclude interfering light.

A further understanding of the nature and the advantages of particular embodiments disclosed herein may be realized by reference to the remaining portions of the specification and the attached drawings.

DETAILED DESCRIPTION OF EMBODIMENTS

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

A performance capture system is provided to detect one or more active marker units in a live action scene. Active marker units emanate at least one wavelength of light that is captured by the performance capture system and used to detect the active markers in the scene. The system detects the presence of the light as a light patch in a capture frames and determines if the light patch represents light from an active marker unit. In some implementations, various active markers in a scene may emanate different wavelengths of light. For example, wavelengths of light from active marker units may be changed due to various conditions in the scene.

The term, "real time" as used herein includes near real time and refers to simultaneous occurrences or occurrences substantially close in time such that they appear to be simultaneous. For example, composited output images may be received by a user in real time, such as within one to three frames, two to four frames, or one to five frames of the capturing of a corresponding picture image during a live action shoot.

The term "frame" as used herein refers to images produced by the components of the visual content generation system. Corresponding images from various components may represent a same frame number or matching frame for a particular moment in time in the live action scene, for example as captured by the image capture device.

A user of the composited output images might be a person who contributes to the making of the visual production. For example, the user may include an individual at the live action shoot, such as a director, a cinematographer, an on-location crew member, an actor, a special effects person, etc. The user may also include an individual responsible for animation of the visual production, such as an artist, a graphics manager, etc.

Figure 1:
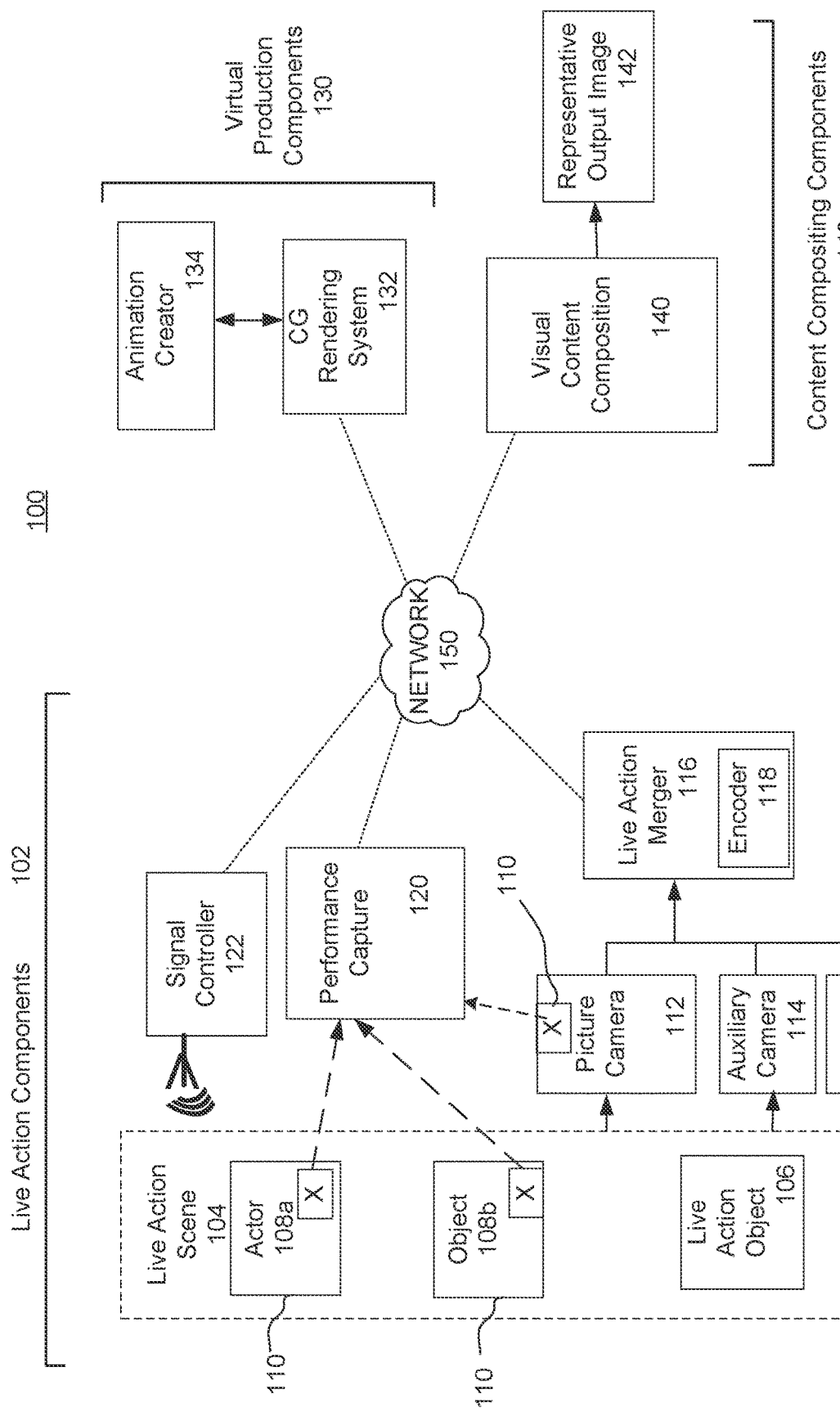
FIG. 1 is a block diagram of an exemplary real time compositing system for generating in real time composited images of visual elements for use in creating a visual production, in accordance with some implementations.

FIG. 1 is a block diagram of an exemplary real time compositing system 100 having various components in which the present performance capture system may be implemented. The components of the real time compositing system 100 include: live action components 102 for generating visual data from a live action scene 104 using the performance capture system; virtual production components 130 for generating CG graphic information; and content compositing components 140 for generating representative output images. The live action scene 104 defines the space available for recording and may include a motion production set, a performing stage, an event or activity, a natural outdoor environment, etc. Any of the system components may communicate with the other components through a network 150 or other data transfer technologies. Although the real time compositing system 100 is described in detail, the present performance capture system may also be implemented in other systems for visual productions and with variations of the real time compositing system 100.

Live Action Components 102

The live action components 102 may include a variety of visual capture devices, including at least one image capture device 112 for capturing live action images of a target object 106 in the live action scene 104, one or more auxiliary capture devices 114, e.g., 3dimensional (3-D) cameras having one or more depth sensors, for capturing auxiliary images (depth images) for use in determining depth data, and a performance capture system 120 for capturing marker images. The image capture device 112 and auxiliary capture devices 114 may communicate with a live action merger system 116 to combine depth data with picture images. The performance capture system 120 is used by the real time compositing system for capturing movements of marker objects 108a, 108b by generating light information from active marker units 110 in the live action scene 102.

The performance capture system 120 may detect light from a plurality of active marker units 110. The active marker units 110 are light devices coupled to marker objects 108a, 108b in and/or adjacent to the live action scene 104 that emanate and/or reflect light of particular wavelength ranges, e.g., infrared. The light is detected by the performance capture system 120, which determines the location and movement of the marker object or part of the marker object. The plurality of active marker units 110 are used as reference points of positions of the respective marker objects 108a, 108b in the live scene. The reference points may be used for replacement with computer generated items.

One or more active marker units 110 may be attached directly to the object or attached to an item on the object, e.g., strap, clothing, shoe, hat, etc. A plurality of active marker units may be coupled to various parts of a marker object, such as a face, foot, or body to track how the object or part of the object moves in the scene. In some implementations, active marker units may be attached to a face of a live actor to detect facial expressions. Marker objects 108a, 108b may include performers, e.g., actors, items, e.g., props, etc., that are intended to be replaced, in whole or in part, with CG elements in output images 142.

In some implementations, the image capture device 112 that may be coupled to one or more active marker units 110. The image capture device location may be tracked through the attached active marker units as the image capture device 112 captures the live action scene 104. Marker data obtained from active marker units 110 on the image capture device 112 may be transmitted, such as through network 150 to the CG rendering system 132 and/or to an animation creator 134.

The plurality of active marker units 110 includes active marker units provided emanate infrared and/or visible light. The light emanated by the active marker unit may be any frequency of electromagnetic radiation. Active marker units 110 may additionally be used to pre-calibrate various devices of the real time compositing system 100. The pulse rate of the light may be calibrated to be consistent with the detection camera exposure time so that light is emanated only when the camera shutter is open. The light may be emanated at regular and even intervals during the duration of the camera exposure time.

The active marker unit may include a plurality of LED's, e.g., a bundle of three LED's. The light source may emanate infrared light. In some implementations, a different wavelength of light or filters may be used for various conditions, such as blue wavelength light for underwater scenes. The active marker unit may include one or more light sources, an inlet/outlet interface for receiving signals and sending data, and a battery. The active marker unit may be any shape that permits emission of light, such as a hemisphere or sphere shape.

The active marker unit may provide benefits in sensitivity and reduced energy requirements over traditional reflective markers. For example, when using reflective markers in an outdoors scene, environmental light may interfere with detection of the reflected visible light. The active marker unit does not experience such extensive distortion of received light. In addition, the active marker unit may use less power than reflective markers because light is only required to travel one way from an active marker units to a detection camera, rather than two-ways to a reflective marker and reflected back.

In infrared active marker systems, the performance capture system 120 may be a camera that includes a visible light filter to block visible light and allow only infrared wavelength light to be detected by the camera sensor. In some implementations, the performance capture system 120 may be computer vision cameras and mono cameras that are sensitive to infrared light, e.g., that exclude infrared blocking filters, or other light sensors.

The performance capture system 120 feeds marker data obtained from the detection of the active marker units 110 to the CG rendering system 132 to be mapped to a virtual model using software of the CG rendering system 132. The CG rendering system 132 may represent the selected active marker units 110 in a virtual environment. For real time performance, the performance capture system 120 may operate at a high rate, such as 120 frames per second ("fps").

Signal controller 122 may release signals to direct an action by the system components such that the real time compositing system 100 components drive capture by one or more a sensor device, e.g., a camera, of the performance capture system 120, configured to capture at least one particular wavelength light from the active marker units, at the same time. In some implementations, signal controller 122 communicates with markers 110 to emanate light for the performance capture system 120, as described below with regard to an "active marker" or "active marker unit." In some implementations, the signal controller 122 emanates radio frequency signals to receivers on various components, such as the active marker units 110, as further described below.

The performance capture system 120 may include any number of sensor devices to detect the light emitted from the active marker units. The sensor device may include a narrow-pass filter to detect a particular wavelength or range of wavelengths of the light emitted from the active marker units. In some implementations, the sensor device may be configured to detect multiple distinct wavelengths of light. For example, a sensor device may include filters to separately detect different wavelengths in an infrared range, or machine vision cameras for ultraviolet wavelengths. In some implementations, multiple sensor devices may be employed with individual sensor devices being dedicated to detecting a wavelength of light.

In some implementations, device parameter data from the image capture device may be accessed in the central storage unit 150 and used to match CG parameters for CG elements in CG images with image capture device parameters, such as perspective, position, focal length, aperture, and magnification, of the CG images. In this manner the CG images may be created in an appropriate spatial relationship with the target objects 106. The image capture device 112 captures picture images from the live action scene 104. The image capture device can be any type of camera for digital cinematography capturing of live action shots, such as professional high end digital cameras or low end consumer cameras for digital cinematography. The image capture device 112 can capture images using different camera parameters. Parameters may include resolution (e.g., 2.7K and 4K), frame rate (e.g., 24 fps, 48 fps, 60 fps and 120 fps), exposure rate (e.g., $1/50^{th}$, $1/100^{th}$, $1/120^{th}$), International Standards Organization (ISO) setting, viewing angle (e.g., 180 degrees), etc.

The auxiliary capture device 114 captures auxiliary images of the live action scene 104 that correspond with picture images of the image capture device 112. For example, one or more auxiliary capture devices, e.g., depth cameras, may be positioned to flank the image capture device and capture auxiliary images of one or more of the same target objects captured by the image capture device at the same time or substantially the same time (e.g., slightly after) that the image capture device captures corresponding images of the target objects in the live action scene. In some implementations, the one or more auxiliary capture devices 114 may include sensors and/or lenses attached to or integrated with the image capture device 112. In some implementations, depth data may be obtained based on the time that light needs to travel from a light source to the object and back to the camera. The light source and image acquisition, e.g., via the depth camera, may be synchronized to extract the distances calculated from the obtained image data.

The auxiliary images are used by the live action merger system 116 to obtain depth data for pixels in the corresponding picture images, for example to generate depth data for target objects 106 in the live action scene 104. The auxiliary capture device 114 may capture the same or similar auxiliary images from the live action scene 104 as the picture images captured by the image capture device 112.

Depth data may include a depth value for a plurality of pixels of the corresponding picture image, and a depth map created with the depth values. For example, each pixel of the corresponding picture image may be associated with a depth value. The depth value is a distance between the image capture device position and a plane that is perpendicular to a viewing direction of the image capture device 112, e.g., direction of image capture device lens. However, in some implementations, the depth value may be referenced from a different camera, rather than the image capture device, and may be calculated to a desired plane or point. The depth values may be used to create a depth map. The depth map may be at the same as or higher resolution than the picture image so that it can be mapped to the picture image to generate a deep live image and provide a depth for pixels in the picture image.

The auxiliary capture device 114 may include a stereo depth camera system having a pair of depth sensors, e.g., "left" and "right" cameras, and calculates stereo depth data per pixel in the picture images to determine depth of target objects 106. Thus, the auxiliary capture device 114 may include any number of cameras, such as two cameras with depth sensors. In some implementations, other approaches to obtain depth data may be used. For example, structured light, time-of-flight, photogrammetry, etc. techniques may be employed.

The auxiliary capture device 114 may have certain operating parameters that are considered for operation under diverse live action scenes. For example, auxiliary capture device 114 should be robust under low lighting scenes, reduce motion blur, produce satisfactory resolutions, operate within required distance ranges, etc. The sensors of the auxiliary capture device may be adjusted to detect depth at a various distances. For example, by widening the distance between the sensors, longer depth distances may be detected and by narrowing distance between the sensors, shorter depth distances may be detected. Longer distance ranges may result in less resolution. In some implementations the resolution of auxiliary images of the auxiliary capture device is the same resolution as the picture images of the image capture device, such as standard 2K resolution, or greater resolution than the picture images.

The auxiliary capture device 114 may be configured to detect depth within a specific distance range, such as half of a meter to five meters, half of a meter to ten meters, etc. If a subject target object that is being tracked by the auxiliary capture device 114 moves outside of the designated distance range, the distance of the subject target object may not be detectable by the auxiliary capture device 114, which may persist even if the subject target object moves back within the designated distance range.

Although the auxiliary capture device 114 is described as being a camera dedicated to obtaining depth data and that is distinct from the image capture device 112, in some implementations, the depth data may be computed from any camera, including the image capture device 112.

Image data from an image capture device 112 and depth data, e.g., depth maps from the auxiliary capture device 114, may be merged by live action merger system 116 to produce deep live images. Deep live images may include a picture image integrated with corresponding depth maps. The deep live images may be compressed by an encoder 118 that may be part of the live action merger system 116 or a separate encoder device. The deep live images may be integrated (also referred to as "composited") with CG data via virtual production components described below, to produce representative output images for viewing during the live action shoot.

An output image display device 124 at the live action shoot may be provided to show the representative output images in real time. The representative output images may be viewed by users, such as creators on location at the live action shoot. For example, a director may view the displayed representative images to determine on the fly whether any changes are needed with the actors, props or set.

In some implementations, the output image display 124 may be a dedicated device, e.g., standalone device, to show the representative output image, such as a handheld device, personal computer, or wearable computer device for an individual user. In some instances, the output image display may include a large screen, e.g., mounted screen, that is near the live action scene and viewable by one or more on-location users. In some implementations, the output image display device 124 may be integrated with one or more other cameras on location at the production shoot, e.g., image capture cameras, auxiliary capture devices, performance capture system, etc. For example, the output image display device 124 may include a split screen on a camera, e.g., a camera view finder, with one side depicting the presently captured picture image and the other side showing a representative output image.

Virtual Production Components

An animation creator 134 is used, e.g., by artists and other users, to specify details, programmatically and/or interactively, of CG elements to be generated by the CG rendering system 132. In some implementations, the CG elements are constructed by the animation creator 134 in real time with the shooting of the live scene and while receiving deep live images and/or performance capture images.

Real time creating of CG elements with use of the deep live images and corresponding performance capture images enables tailoring of the CG elements to the corresponding live scene to create a realistic spatial and timing relationship between CG elements and target objects. By contrast, when CG elements are created and recorded during a pre-production stage, the CG elements are played back with the live elements and marker objects are replaced with the CG elements. However, the characteristics of pre-productions CG elements may be locked-in such that changes in the live action scene 104 may create a mismatch with the CG elements. Distorted views of the CG elements in context of the live action shoot, such as timing changes in the live scene, may require post-production editing of CG elements or further takes of the live action shoot.

The animation creator 134 and CG rendering system 132 may include computer processing capabilities, image processing capabilities, one or more processors, program code storage for storing program instructions executable by the one or more processors, as well as user input devices and user output devices, not all of which are shown in FIG. 1.

The CG rendering system 132 may receive the deep live image from the live action merger system through network 150 and decompress encoded image data. The CG rendering system may produce CG elements that complement features of the live action scene 104. For example, the CG rendering system 132 may determine lighting, shadowing, and shading that are consistent with the features of the live action scene 104 as provided in the deep live image. With real-time feeding of live action data to the CG rendering system 132, creators of the live action shots can change compositional aspects of a shot, such as lighting, focal length, e.g., zoom, on the fly and in response, the animation creator 134 and/or the CG rendering system can make real time adjustments in the CG images. For example, CG elements may be adjusted to maintain focus and proper lighting in the output images 142. With the depth data of the target objects provided by the deep live image, the CG rendering system 132 may determine characteristics needed in the CG image to create a realistic appearance to an extent specified by the visual production. For example, if a light source, e.g., the sun, is located behind a CG element, the CG system may include in the CG image, a shadow made by the CG element. Similarly, the live shot creators may adjust light position and intensity on the set to match with CG images to assist in a realistic appearance.

In some implementations at least one central storage unit 150 maintains production information, such as in one or more production databases Production information includes data related to a particular production shoot. Such information may include capture device parameters and/or performance capture system parameters (such as perspective, position, focal length, aperture, contrast, focus, exposure, and magnification) that are employed during capturing of particular images. Where parameters are adjusted, such as sensor device parameters to fix on one or a group of light patches, the updated parameters may be maintained in the central storage unit 150. Production information may also include object information related to objects in a live action scene, such as identification of target objects in the live action scene and their part in the scene, types of target objects, call sheets, identification of performance capture active marker units, marker locations, unique identifiers of corresponding images and data, etc. For example, production information may include records of target objects and/or CG elements in the scene. There may be numerous target objects and CG elements scripted to be in a photo shoot that is required to be tracked. Real time tracking of updates of the production information is a valuable asset in streamlining the creation of a visual production. Production information may further include identifiers of corresponding images and data, as described below.

Use of the central storage unit may conserve resources that may be otherwise necessary if each component of the real time compositing system 100 is required to determine, store, and track the production information. For example, the performance capture system 120 may access and use production information to identify the live action actors and assist in identifying marker locations. In another example, the CG system may access and use production information identifying CG elements for creating of the CG elements and integrating CG elements with target objects.

The storage unit 150 may be dynamically updated, e.g., during scheduled intervals or when objects/elements associated with the production information have been changed. The updated production information may replace existing information. In some implementations, the updated production information may be added and marked as current production information, so as to maintain a history of the prior outdated production information. In this manner, a creator of the visual production may opt to undo the update to return to the prior production information or otherwise refer to the outdated information.

The central storage unit 150 may be configured to receive updated production information from the various components of the real time compositing system 100 and/or via other components, e.g., computing devices used in direct communication with the central storage unit 150. Updated production information may reflect alterations made in response to one or more users viewing the display of the representative output image. Such updates to production information may be made on the fly during the live action shoot as the representative output image is viewed by users. The updates may be pushed out in real time to components of the real time compositing system 100.

In some implementations, the CG rendering system 132 may segment CG elements of a CG rendering intended for an output image 142. Individual CG elements or any combination of CG elements may be rendered as separate respective CG images. Multiple CG images, such as three to four CG images, may be merged in generating the output image 142.

In some implementations, particular CG elements may be excluded from the representative output image and added in post-production editing for generate a final output image for inclusion in the visual production. For example, if a live actor is wearing virtual glasses and takes the virtual glasses off, the glasses may be added into the representative output image. However, reflections on the glasses may be added in post-production to produce a realistic look.

Content Compositing Components

A visual content composition system 140 may sync information, e.g., images and data, produced at various times from multiple components of the real time compositing system 100, such as image capture devices 112 at a live action scene, auxiliary capture devices 114 for depth data, performance capture system 120 for marker data, and production information stored in the central storage unit 150. The visual content composition system may identify corresponding images and data associated with particular time blocks. The visual content composition system 140 may provide the identification information to various components, e.g., the CG rendering system 132. For example, corresponding images and data may be marked with a unique identifier that may be used to associate the corresponding images and data, e.g., associated with metadata that includes the identifier.

The deep live images from the live action merger system 116 and CG elements from CG rendering system 132 may be fed to the visual content composition system 140 for integration by a live composition application. The visual content composition system 140 matches CG images having the CG elements, with the deep live image to overlay the CG view and live action view on top of each other and generate representative output images 142, while the live action scene 104 is in motion. The representative output image 142 is rich in detail from the use of the supplemental data in the composing of the representative output image 142. In some implementations, more than one CG image is provided and each CG image has a different CG element, e.g., CG item. Multiple CG images may be composited with a deep live image by the visual content composition system 140 determining pixel locations for each of the different CG elements. For example, particular pixels of the deep live image may be replaced with particular pixels in the CG image. Aligning of the CG image data and the deep live image also includes synchronization of frames and data as the images are produced.

The compositing process by the visual content composition system 140 is performed in real-time such that each frame is composited and ready for display at a standard frame rate being used for playback (e.g., 30 or 24 fps, etc.). It is desirable to reduce any delay between an image acquisition and display of a composited output image. In some implementations the rate of the compositing process is the same as the image capture device 112 frame rate. Rate of the compositing process may depend on various rate specifying factors, such as a rate that the hardware (e.g., camera) supports, broadcast standards, and particular affects required by the particular visual production. In some implementations, frames may be skipped, or dropped, or the compositing modified to be slower for some of the images than real time, while still achieving desired functionality.

The visual content composition system 140 is a representation of various computing resources that can be used to perform the process actions and steps described herein. Any number and type of discrete or integrated hardware and software components may be used. The components may be located local to, or remote from the other system components, for example, interlinked by one or more networks 150.

The network 150 may include a public network (e.g., the Internet), a private network (e.g., a local area network (LAN) or wide area network (WAN)), a wired network (e.g., Ethernet network), a wireless network (e.g., an 802.11 network, a Wi-Fi network, or wireless LAN (WLAN)), a cellular network (e.g., a long term evolution (LTE) network), routers, hubs, switches, server computers, or a combination thereof.

In some implementations, the visual content composition system 140 renders the representative output image for real time feedback information. The representative output image may be rendered at a particular rate for display, such as 24 fps or 30 fps. In some implementations, the visual content composition system 140 is dedicated to produce the representative output image 142 and a different renderer produces a final output image that is included as content in a final visual production.

The representative output image 142 may be substantially similar to the final production image, or may be the same as the final production image. For example, the representative output image 142 may undergo final adjustments and editing prior to finalizing the image.

The representative output image 142 may be provided to a live actor creator, such as a director, through the output image display device 124 having a display screen. The representative output image may be displayed in a 2-D or 3D format. In some implementations, the representative output image 142 may be provided to a view finder of the output image display device 124 during the live action shoot. For example, a display on the image capture device may show the representative output image 142 during the production shoot. In some implementations, an on-location user, e.g., a director of the production shoot, may view both the representative output image 142 and the picture image being captured by the image capture device 112 during the production shoot. For example, the output image display may be a split screen with one side depicting the presently captured picture image and the other side showing the representative output image. However, the director may choose to focus attention onto the representative output image 142 because the picture image may provide insufficient detail for the director. The picture image lacks the CG elements. In some implementations, the output image display device 124 may be a dedicated display device for the representative output image, such as a handheld device, personal computer, or wearable computer device for an individual user, or may include a large screen, e.g., mounted screen, that is near the live action scene and viewable by one or more on-location users, The image capture device 112, auxiliary capture device 114, and performance capture system 120 may have different lengths of time in which the respective sensors of the individual devices are exposed to light to capture images. The encoder 118 also may process deep live images at a particular rate. As a result of the different exposure and processing times, the arrival times in which the respective images are received by the downstream components in the composition process varies accordingly. In order to align corresponding images, the real time compositing system 100 may account for the image arrival times.

In order to synchronize the corresponding incoming visual data from its various sources, holding times in a number of frames may be determined for the particular capture and processing devices. For example, the CG rendering may be configured to delay processing of CG images, e.g., hold one to three frames, for slower frame rates of an image capture device. For example, deep live action image from the live action merger system 116 may be one and a half to three and a half frames lag in being received by the visual content composition system 140.

In some implementations time stamps may be associated with the images and used to track images and to match corresponding images, e.g., timecode metadata, such as SMPTE (Society of Motion Picture and Television Engineers). In some implementations, aligning the visual data by timestamps, e.g., timecodes, from the capture devices alone may result in inaccurate alignment, due, at least in part, to the different exposure times of the capture devices. For example, the performance capture system may operate at high speeds such that more than one frame (e.g., 2 frames) is stamped with a same time code.

The components of the real time compositing system 100 may use processing times and other camera parameters to determine matching frames received from upstream components. Exposure times and/or frame rates of the various cameras may be used to calculate expected arrival times for respective images at a receiving component and to identify corresponding images. For example, images of an image capture device 112 having an exposure time of $1/48$ second may be expected to arrive at the live action merger system 116 slower than an auxiliary capture device 116 that has an exposure time of $1/100^{th}$ second. The respective image arrival times are determined and images matched to create a deep live image. Images arrive to the CG rendering system 132 from upstream components, a performance capture system 120 and the live action merger system 116 and/or encoder 118. When the a performance capture system 120 has an exposure time of $1/1000^{th}$ second, marker images may have an expected arrival time sooner than deep live images arriving from the live action merger system 116 and/or encoder 118. The different expected arrival times are calculated and corresponding images may be tagged, e.g., identifier, accordingly.

In some implementations, the storage unit 150 may include a checker board type of chart or other data structures for storing, organizing, and comparing image parameters that may be used to synchronize images, such as images from the image capture device 112 and auxiliary capture device 114 may be synchronized. The storage unit may include the identifier of corresponding images with the production information to associate production information with the corresponding images. Updated production information may include changes to capture device parameters or object information associated with deep live images currently or recently received by the visual content composition system.

Updating of the production information in the central storage unit 150 may trigger pushing out of the updated production information to the visual content composition system and/or other components. In some implementations, a notification of the updates may be sent to the components and the notification triggers the components to access the stored updates.

Performance Capture System with Active Marker Units

In some implementations, one or more of the various markers 110 detected by the performance capture system 120 include active marker units having one or more light sources.

Active markers provide benefits in sensitivity and reduced energy requirements over traditional reflective markers. Traditional reflective markers use a camera with a light source having a specific wavelength, such as a ring light with infrared LED light. The light source on the camera may emanate light when the shutter of the camera opens at the time of the synch pulse. The reflective markers have reflective material that reflects the received light from the camera back to be detected by the camera.

Active markers enable improved detection of light over reflective marker technology. For example, when using reflective markers in an outdoors scene, environmental light may interfere with detection of the reflected light. The reflected light may decrease with the square of distance. For example, for a marker placed at 10 m from a detection camera and that reflects 100% of light, the amount of light reflected may drop off 100 times as it travels to the detection camera. The active marker does not experience such extensive distortion of received light. In addition, the active marker may use less power than reflective markers because light is only required to travel one way from the marker to detection camera, rather than two-ways to the marker and reflected back.

Figure 2:
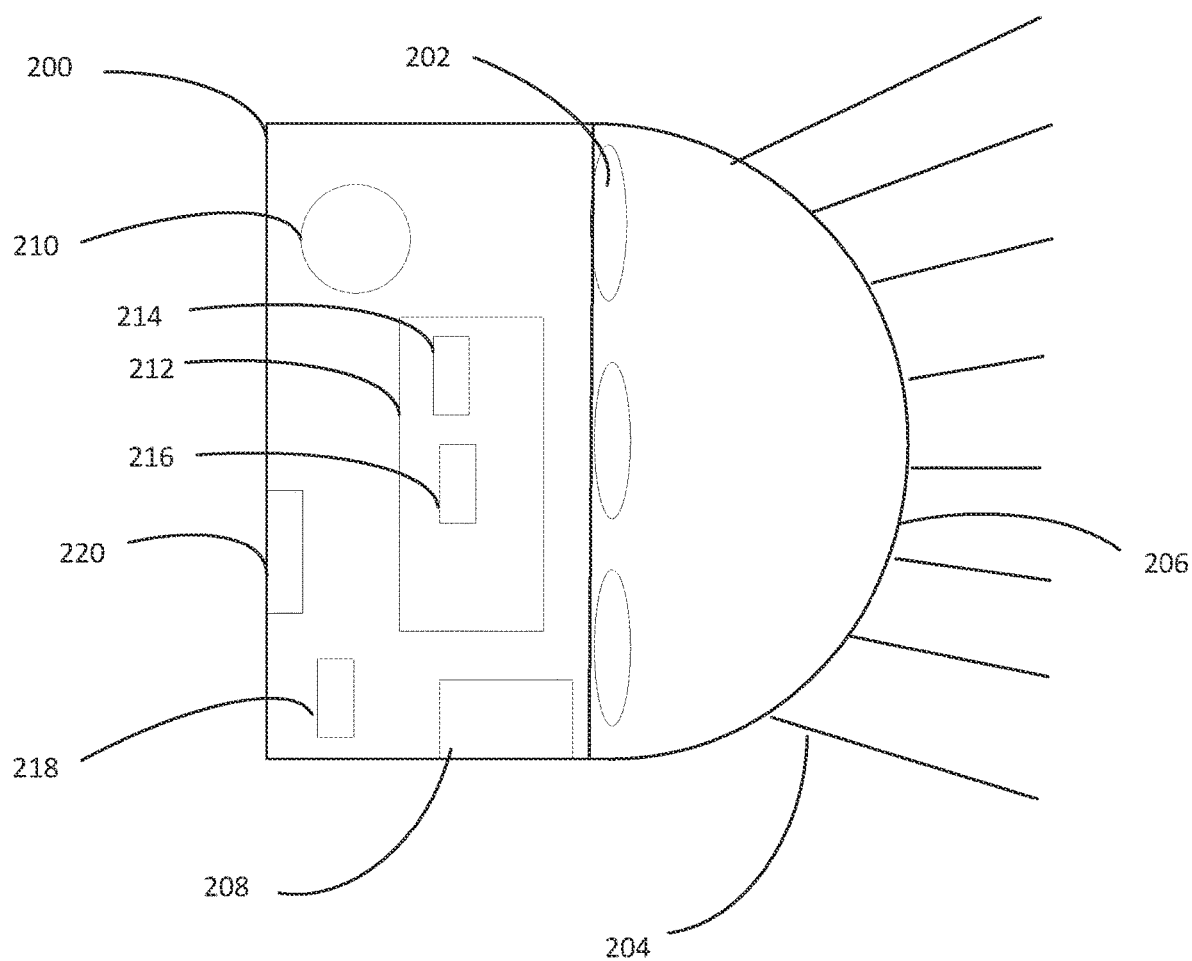
FIG. 2 is a schematic diagram of an exemplary active marker unit, in accordance with some implementations.

FIG. 2 is a schematic diagram of an exemplary active marker unit 200 including light sources 202, such as an LED or an array of a plurality of LED's 202 (e.g., a bundle of three LED's). The light 204 from the light sources 202 passes through a diffuser 206, which includes at least one surface that is transmissive to the wavelength of light emitted by the light sources 202. In some implementations, the active marker unit may be fully or partially self-contained to include one or more of an inlet/outlet interface 208 for receiving signals (e.g., receiver) and sending data (e.g., transmitter), drive electronics, and a battery 210.

The diffuser 206 may be any shape that enables detection of a wavelength or a range of wavelengths of light passing through the diffuser, such as hemisphere or sphere shape. In some implementations, the diffuser 206 enable controlled disbursement of light through various surfaces of the diffuser that have different transmissivity properties for assorted wavelengths of light. For example, a portion of the diffuser 206 may be transmissive to a first wavelength range of light and block other wavelengths of light. A separate portion of the diffuser 206 may be transmissive to a second wavelength range of light but block other wavelengths (e.g., the first wavelength range). In this manner, the diffuser 206 may serve as a filter to selectively permit one or more particular wavelengths of light to emanate from the active marker unit. In some implementations, opaque portions of the diffuser 206 may block light emitted from the light sources, such that the light only diffuses through the transmissive surfaces of the diffuser 206. In this manner, light may be directed to emanate from the active marker unit in particular directions and/or to form specific shapes of light points for detection. In some examples, a periphery of the diffuser may be opaque to focus the light to disperse from a central transmissive portion. Focusing of light by the diffuser may avoid light reflecting off of the object to which it is attached or other leakage of the light.

The light source 202, which emits light for detection, may be one or more infrared LED's, e.g., between 700 nm and 1 mm, or more specifically between 800 nm and 960 nm. For example, the light source can be a 940 nm wavelength, 1 watt infrared (IR) LED. However, other light sources are possible, such as ultraviolet light source and the sensor device is an ultraviolet detector. In some implementations, various wattage light sources may be employed depending on the live scene of the shoot. For example, higher wattage may be used when shooting in bright daylight and lesser wattage for dark scenes.

In some implementations, a different wavelength of light or filters, or combinations of different wavelengths may be used for various different active marker units in a scene, under various conditions, such as blue wavelength light for underwater scenes. In some implementations, a live action scene may include multiple markers that emanate different wavelengths of light. For example, an object may include groups of active marker units that each disperses distinctive wavelengths of light.

In some implementations, a multi-emitting active marker unit may be configured to emanate different wavelengths of light at various times. For example, at first time period one wavelength or range of wavelengths of light may emanate from the multi-emitting active marker unit. Then at a second time period a different wavelength or range of wavelengths of light may emanate from the same multi-emitting active marker unit. The multi-emitting active marker unit may be controlled to emanate particular wavelengths of light based on various factors, such as environmental conditions, sensor technology employed to capture the light, according to a pre-defined time schedule for the various wavelengths of light, for a particular scene and/or object being shot, etc.

In some implementations, one or more multi-emitting active marker units may emanate different wavelengths of light at the same time. For instance, a first wavelength of light may emanate from one part of the multi-emitting active marker unit, such as a front side, and a second wavelength of light may simultaneously emanate from a different part of the multi-emitting active marker unit, such as a backside. The multi-emitting active marker unit may include multiple light sources, e.g., LEDs for infrared light, for example, and other light sources for visible light or ultraviolet light. In some implementations, the different types of light sources may point to different areas of the multi-emitting active marker unit to emanate from different sides. The distinctive types of light sources may be separately controlled to emit light during different time periods or at the same time. For example, the control unit may actuate various components of the multi-emitting active marker units to emit particular wavelengths of light.

In some implementations, a sensor on the active marker unit or associated with the active marker unit may determine target light parameters suitable for a current condition and the wavelength of light may be changed based on the condition. Light parameters may include wavelength of light, intensity of light, strobing pattern of emanating light, etc. Functions of one or more active marker units may be adjusted according to the target light parameters, such as, emanating a particular wavelength of light, increase or decrease in intensity of the light, increasing or decreasing a portion of diffuser that permits light to emanate or other techniques to change the size of a captured light patch, etc. Sensors may be employed to detect conditions, such as a higher than threshold amount of interfering light, moisture conditions, distance between the active marker unit and a detecting sensor device. Other conditions, light parameters, and functions are possible.

In some implementations, the different wavelengths of light may be captured by different sensor devices. In some implementations, one sensor device may include separate components to detect two or more different wavelengths of light by the same sensor device.

The pulse rate of light emanating from the active marker unit may be in synch with global shutter signals and according to the signal controller 122. For example, the pulse rate may be calibrated to be consistent with the detection camera exposure time so that light is emitted only when the camera shutter is open. The use of a pulse rate rather than constant emitting of light may provide a benefit in reducing energy needs and on-board battery life. The light may not be emitted when a camera shutter is closed and light is undetected.

The active marker unit and/or control unit may be placed at a distance that enables receiving of signals from the signal controller 122 and detection of light by the detecting camera, e.g., performance capture system 120. For example, the active marker unit and/or control unit may be located up to 50 m from the signal controller 122.

The active marker unit may be controlled remotely by a wireless system, such as signal controller 122 through the I/O interface 208 on the active marker unit, to synchronize with a global synch pulse by the signal controller 122. The sync signal may operate in a low bandwidth, e.g., a ZigBee communication system operating at a 900 megahertz or 915 Mhz range signal and narrow bandwidth, e.g., less than 20 Khz, in compliance with power regulations for the band. The sync signal may use radiofrequency to transmit information. In some implementations, the pulsing of light sources on the calibration marker and the other markers located on items in the scene, including the image capture device are controlled by a signal controller 122. In some implementations, the pulse rate of the active marker unit may be at a variety of rates relative to frame rate of the detection camera, such as light emission every other frame, and more than once per frame. In some implementations, the light may be emitted at regular and even intervals during the duration of the camera exposure time.

The strength of the light, power, pulse rate, and duration of each light pulse may depend of various factors, such as distance, environmental light conditions, etc. In some implementations, the active marker unit may include a computer device 212 having a processor 214, that performs operations for instructions stored in memory 216, for example for controller 218 to direct the emitting of light at a pulse rate according to received signals. The logic may enable dynamic determining various target light parameters suitable for current conditions and controlling of the function of the active marker unit to the target light parameters, such as a target length of time for the light pulses (e.g., 0.5 msec., 2.0 msec., or 4.0 msec.), an intensity amount, etc., and may adjust the parameters accordingly on the fly. For example, light intensity may be increased when the marker is exposed to bright light (e.g., outdoor lighting) situations. In another example, the active marker unit or control unit may be configured to detect a low battery condition and switch to a power conservation mode, and/or send an alert to system components, such as the signal controller 122 and/or performance capture system 120.

The signal controller 122 may send various parameters to the active marker unit, such as power settings and light pulse durations. The parameters may also include commands to change modes such as from active to sleep mode. In some implementations, the signal may be encoded and an identification key may be sent to a receiver (e.g., I/O interface 208) on the active marker unit before signals are emitted. In this manner, the active marker unit may be enabled to identify signals from the signal controller 112 and ignore (not respond to) background signals.

In some implementations, the active marker unit may send information to the signal controller 122 through the I/O interface 208 and the signal controller 122 may include a receiver to receive information from the active marker units. For example, the active marker unit may provide an alert message or signal to the signal controller 122 and/or performance capture system 120 in case of an event (e.g., adverse condition), such as low battery or other conditions that may affect function. The alert may trigger the active marker unit and/or controller to change the wavelength of light being emitted.

The active marker unit may be locally powered. For example, the active marker unit may include a battery 210, such as a non-rechargeable or rechargeable coin cell battery. In some implementations, the battery 210 provides in-use time of two hours or more and standby time of at least two days.

In some implementations, an activation system may be used that may turn on and/or off the active marker unit, especially in particular situations, such as when a marker is out of range or out of field of view of the detection camera, e.g., the performance capture system 120, or otherwise undetectable such as when the light source of an active marker unit faces away from the detection camera. For example, a hemispherical shaped active marker unit may rotate away from the detection camera to face a back area. The activation mechanism may include an activation light, e.g., a strobe light from a single light source, provided by a device, such as the performance capture system 120. The activation light may be received by the active marker unit, e.g., by a diode 220, and the active marker unit may turn off its light source when the activation light is not detected. In this manner, power may be conserved by the active marker unit.

In some implementations, a plurality of active marker units that are may be provided in the live action scene. The plurality of active marker units may emanate the same or similar type, amount, and pulse rate of light. The individual active marker units may be indistinguishable by comparing light released. For example, all of the active marker units may pulse light at the same rate as the detection camera exposure time, e.g., 1.0 msec., such that light source is switched on to emit light by each active marker unit only during the time period that the shutter is open and turn off to not emit light when the shutter is closed. In this manner, less information may be needed to detect and process light received from each active marker unit than systems in which each markers pulse in different patterns. For example, only a portion of the exposure time e.g., the time period when the shutter initially opens, may be needed to detect an active marker unit light, such as the first $1/6^{th}$ of the exposure time.

Less information may be acquired and less memory may be needed to store information from shorter processing times, e.g., 4 bits of information.

Furthermore, for active marker units that emanate constant light, e.g., over 1 msec., during a full duration or substantially full duration of an exposure time of a detection camera, e.g., 1 msec., detectability of light may be greater, as compared to patterns of light for shorter periods. In some implementations, the light may be emitted at regular intervals of uniform lengths during the exposure time of the detection sensor. Under some live action scene conditions, environmental light, such as outdoor daylight, may interfere with lights sources that emit shorter sequences of light.

The performance capture system detects a particular active marker unit by the detected an appearance of the particular wavelength of light emanating from the active marker unit in a predesignated detection frame of the performance capture system, regardless of the amount of light emitted, e.g., number of photons, by the active marker unit over a given time block. A trigger threshold of light causes the system to register that a presence of light from an active marker unit is detected. The trigger threshold of light may include a level of contrast of illumination or light intensity of the pixels of the light patch compared to an intensity of an area of pixels, e.g., one or more pixels, surrounding the light patch in an image captured by the performance capture system. In some implementations, the present performance capture system need not quantify a value for an intensity of light to determine a presence of light, but rather uses a comparison of the pixels representing the light with pixels proximal to the light pixels. Thus, the present performance capture system enables a simplified technique to detect active marker light. In some implementations, the trigger threshold may be a threshold size of the light patch captured in a given time block.

Figure 3:
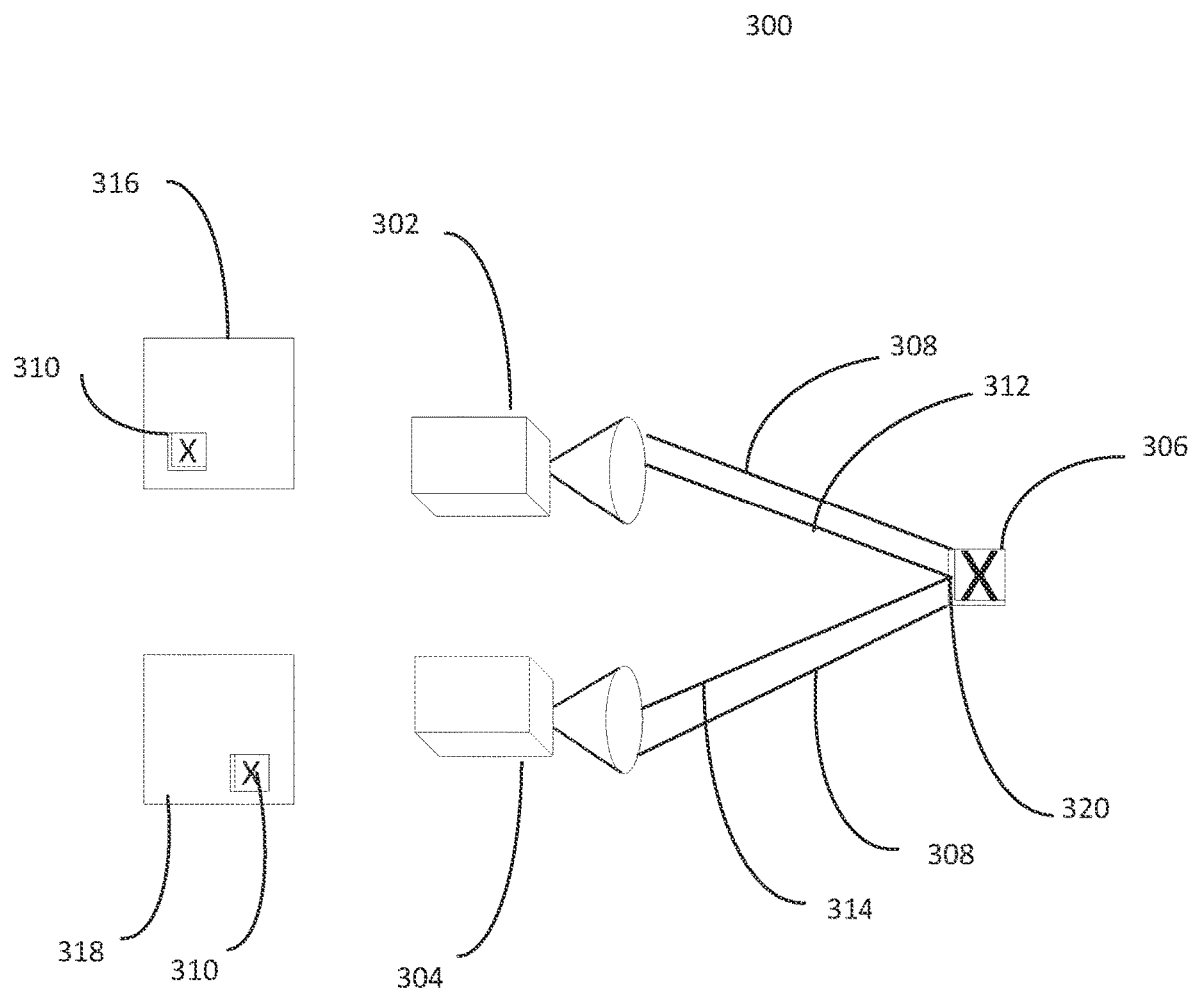
FIG. 3 is a conceptual diagram illustrating of an exemplary active marker identification system, in accordance with some implementations.

In some implementations, individual active marker units in the live action scene may be identified by analyzing the images of the detection cameras and reconstructing marker locations. For example, as shown in FIG. 3, a marker identification system 300 may be used that includes two or more detection cameras, e.g., cameras of the performance capture system 120, including a first detection camera 302 receiving light 308 from active marker unit 306 and a second detection camera 304 receiving the light 308 from active marker unit 306, may be employed to view light emanated from an active marker unit 306. The detection cameras 302, 304 are calibrated to each other. In the respective images 316, 318 of the light source, the depicted light source 310 is in different locations according to the position of the cameras. A first imaginary ray 312 may be drawn from the first to the point of detection of the light source of active marker unit 306 and a second imaginary ray 314 may be drawn from the second detection camera 304 to the light source. Intersection of the rays at the point 320 at the light source indicates a same light source is detected by each of the cameras 302, 304.

The identification process may be performed to identify other active marker units in the scene to determine active marker unit locations. Each active marker unit location may be related to other active marker locations and an arrangement of active marker unit may be reconstructed. The reconstructed arrangement may be matched with predefined marker arrangements stored in a database of marker objects to identify the active marker units and marker objects in the live action scene.

Figure 4:
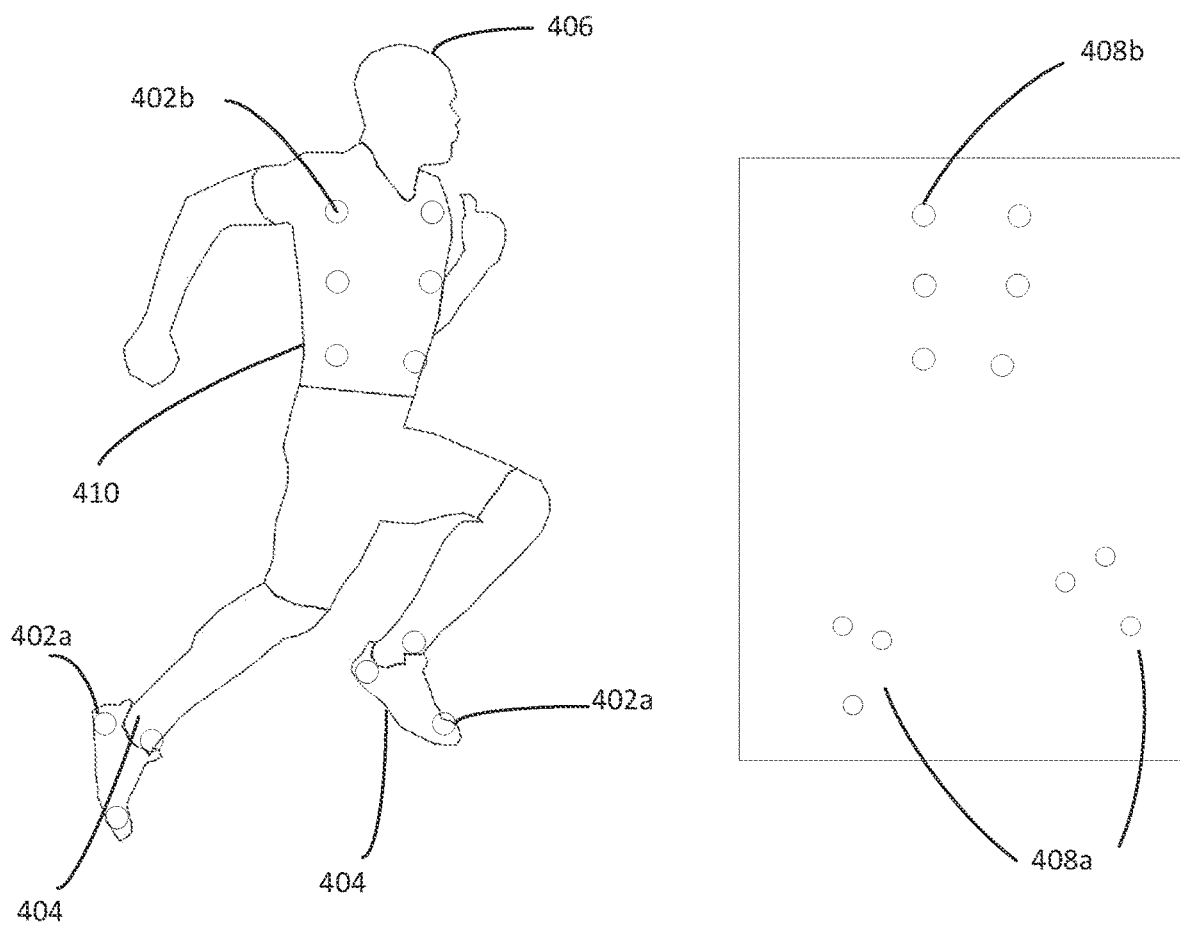
FIG. 4 is a conceptual diagram illustrating a plurality of markers on a live action object, in accordance with some implementations.

FIG. 4 is a conceptual diagram of a plurality of active marker units, coupled to various parts of a marker object. A first set of active marker units 402a are arranged on each of a left and right, foot and ankle parts 404 of a person 406. The first set of active marker units 402a emanates a particular wavelength of light. A second set of active marker units 402b are positioned on a shirt 410 of person 406. In some implementations, the light emanating from the second set of active marker units 402b is different and distinguishable from the wavelength of light from the first set of active marker units 402a. The performance capture system 120 determines a marker arrangement 408a for the first set of active marker units 402a and another marker arrangement 408b for the second set of active marker units 402b. The marker arrangements are determined from the positions of the detected respective wavelengths of light.

In some implementations, a calibration marker may be provided in the live action scene 104 for calibration of capture devices. The calibration marker may be moved, e.g., waived, in various locations in the live action scene 104 for the marker cameras to detect the markers and optimize. The image capture device and/or depth cameras, may also be optimized with the calibration marker by the cameras detecting visible light emitted by the calibration marker in addition to the performance capture system detecting infrared light emissions. The calibration marker may be any convenient shape and size that may emit light, such as a wand that may be handheld.

In some implementations, the calibration marker may use a large amount of power, e.g., 10× typical power of an active marker unit, as described above, for a short period of time. In this manner, motion blur may be reduced or avoided when the calibration marker is quickly moved in the action scene. Furthermore, the light sources on the calibration marker may be detected by the marker camera at long distances, such as 100-200 feet, and in bright light environments in the live action scene 104.

In some implementations, a phase lock device may be employed to synchronize capture devices, such as the image capture device 112, depth cameras 114, performance capture system 120, etc. The phase lock device may be used for wireless syncing of the timing and other parameters of camera devices by generating a reference block. The phase lock device may take large sample sizes, such as 1000 samples, to adjust parameters, such as the phase, time code, broadcast sync standard, through the lens (TTL) metering, performing at rate or a multiplier of the rate (e.g., 24 fps and 24 fps timecode). The copy of the reference signal may be used to calibrate other devices based on the reference block. For example, a device may be calibrated at a multiple of the rate of the reference block, e.g., twice the speed of the reference block, synchronize to the same speed or time code as the reference block, to a square wave, etc.

In some implementations, the light sources may include visible light, infrared, or a combination of light sources, such as visible light and infrared. For example, the calibration marker may include six visible light sources and four to six infrared light sources. The image capture device 112 may detect only the visible light sources and not detect infrared light sources.

In some implementations, the image capture device 112 includes one or more markers 110, e.g., infrared markers, that are detected by the performance capture system 120. The markers 110 on the image capture device 112 enable determination of the position of a lens of the image capture device 112.

Calibration of the image capture device 112 with the performance capture system 120 may be achieved by the image capture device detecting visible light and the performance capture system detecting the infrared light of the marker 110 on the image capture device. In some implementations, calibration of the image capture device, depth cameras, and the performance capture system may be performed prior to the live action shoot. Calibration of the image capture device enables tracking of the position of the image capture device during the performance shoot. In some implementations, tracking information of the image capture device and/or depth camera, may be provided to the CG rendering system so that the virtual camera and the image capture device are consistent in space.

Figure 5:
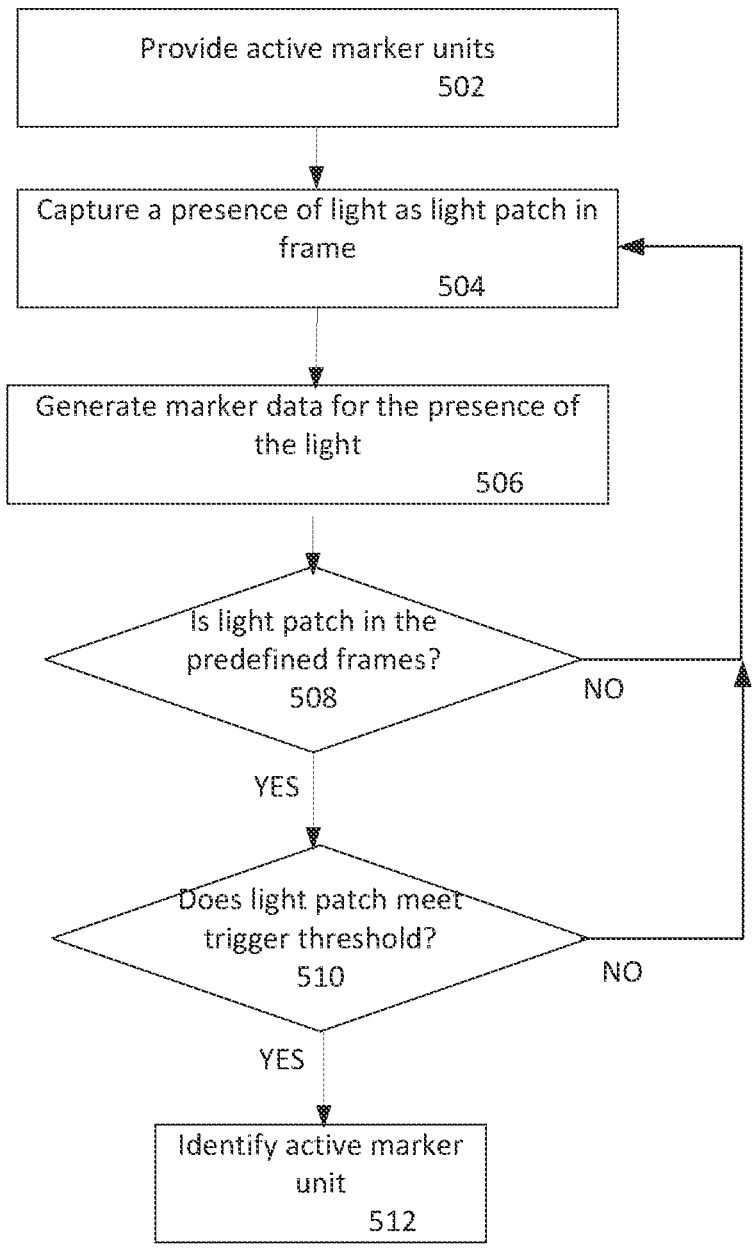
FIG. 5 is a flowchart of an example method for detection of active marker units in a performance capture system, in accordance with some implementations.

The flowchart in FIG. 5 shows an example method to detect active marker units 500. In block 502, the active marker units are provided on an object in the live action scene. The active marker units are configured to emanate at least one wavelength of light in response to signals received from a signal controller.

In block 504, at least one sensor device captures a presence of the at least one wavelength of light emanated by the one or more active marker units in a capture frame produced by the performance capture system.

In some implementations, at least one sensor parameter of a sensor device may be adjusted to fix on the light patch. The sensor parameters may include aperture, contrast, focus, exposure, etc. In some implementations, to further fix on the light patch, a pixel area surrounding the light patch may be masked to exclude interfering light that is not part of a light patch.

In block 506, one or more processors of a computing device of the performance capture system generate marker data associated with the captured presence of the wavelength of light.

In decision blocks 508 and 510, it is determined whether certain criteria are met according to the marker data, to lead to a determination that the light patch represents an active marker unit or group of active marker units. In decision block 508, it is determined whether light patch is present in one or more predefined frames of the performance capture system. This criterion is met if the capture frame corresponds with the predefined frame in a block of time expected to include light emanating from the active marker unit(s) and the process proceeds to determining the next criterion in block 510. If the marker data indicates that the capture frame fails to correspond with the predefined frame, the process proceeds back to block 504 to continue to capture the light.

In decision block 510, it is determined whether the marker data indicates that the presence of the at least one wavelength of light meets a trigger threshold of light in the predefined frame. The presence of the light may be determined by a comparison of the light patch to the background area of pixels proximal to, e.g., surrounding at least one portion of the light patch. There is no need to quantify a value of the light above a minimum threshold that triggers recognition of the light from the active marker unit. If the marker data indicates that the light fails to meet the trigger threshold of light, the process proceeds back to block 504 to continue to capture the light. If the trigger threshold of light is met, based on the marker data, the process continues to block 510 in which the active marker unit is detected by the one or more processors the active marker unit or group of active marker units may be identified.

According to one embodiment, the techniques described herein are implemented by one or generalized computing systems programmed to perform the techniques pursuant to program instructions in firmware, memory, other storage, or a combination. Special-purpose computing devices may be used, such as desktop computer systems, portable computer systems, handheld devices, networking devices or any other device that incorporates hard-wired and/or program logic to implement the techniques.

Computer Device

Figure 6:
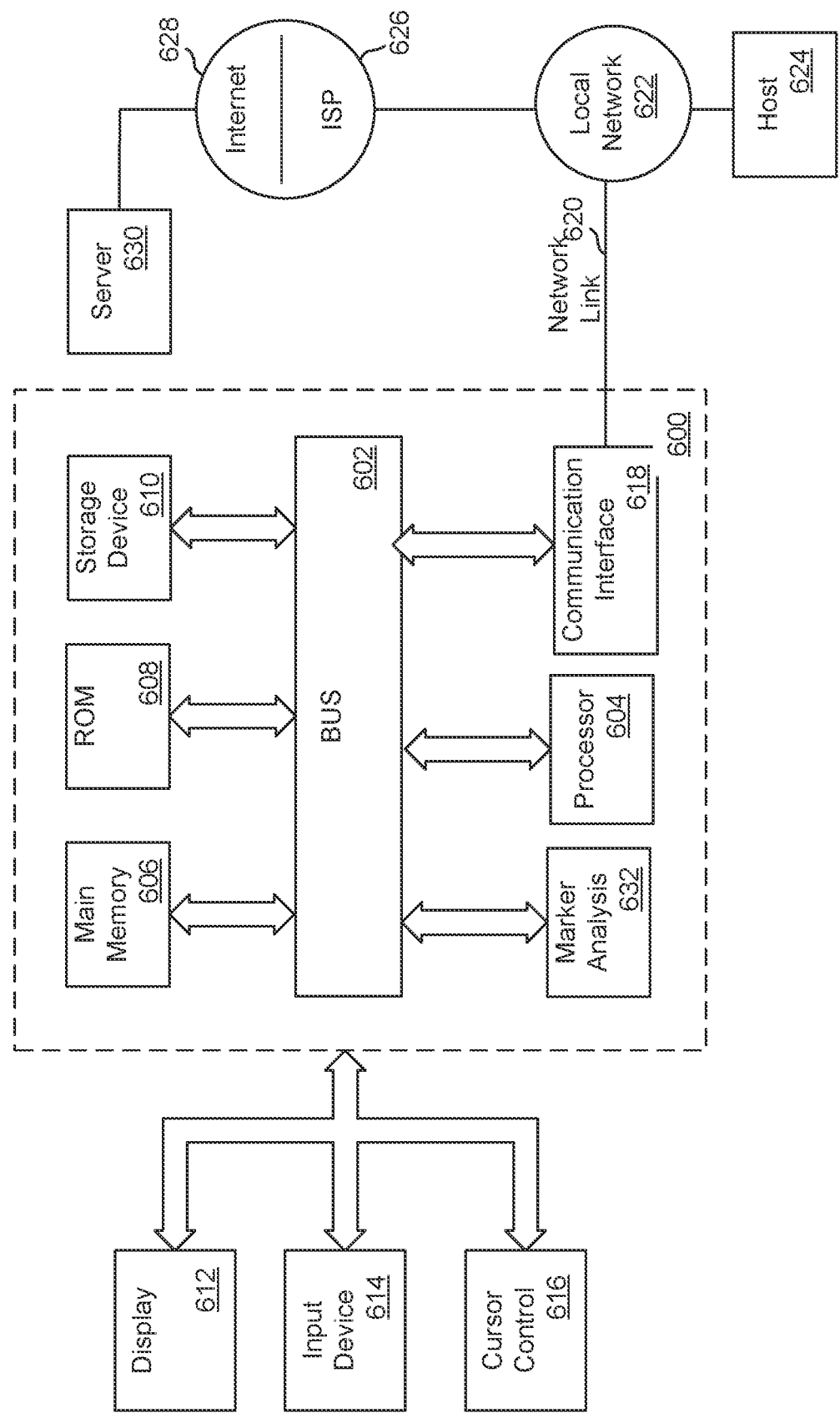
FIG. 6 is a block diagram illustrating an example computer system upon which computer systems of the systems illustrated in FIGS. 1 and 7 may be implemented.

As shown in FIG. 6, a computer system 600 may be employed upon which the performance capture system (such as 120 in FIG. 1) may be implemented. The computer system 600 includes a bus 602 or other communication mechanism for communicating information, and a processor 604 coupled with the bus 602 for processing information. The processor 604 may be, for example, a general purpose microprocessor. The computer system 600 may include a marker analysis component 632 to determine whether the marker data meet criteria and determine a captured light patch represents an active marker unit (for example, items 508, 510, 512 of FIG. 5).

The computer system 600 also includes a main memory 606, such as a random access memory (RAM) or other dynamic storage device, coupled to the bus 602 for storing information and instructions to be executed by the processor 604. The main memory 606 may also be used for storing temporary variables or other intermediate information during execution of instructions to be executed by the processor 604. Such instructions, when stored in non-transitory storage media accessible to the processor 604, render the computer system 600 into a special-purpose machine that is customized to perform the operations specified in the instructions.

The computer system 600 further includes a read only memory (ROM) 608 or other static storage device coupled to the bus 602 for storing static information and instructions for the processor 604. A storage device 610, such as a magnetic disk or optical disk, is provided and coupled to the bus 602 for storing information and instructions.

The computer system 600 may be coupled via the bus 602 to a display 612, such as a computer monitor, for displaying information to a computer user. An input device 614, including alphanumeric and other keys, is coupled to the bus 602 for communicating information and command selections to the processor 604. Another type of user input device is a cursor control 616, such as a mouse, a trackball, or cursor direction keys for communicating direction information and command selections to the processor 604 and for controlling cursor movement on the display 612. This input device typically has two degrees of freedom in two axes, a first axis (e.g., x) and a second axis (e.g., y), that allows the device to specify positions in a plane.

The computer system 600 may implement the techniques described herein using customized hard-wired logic, one or more ASICs or FPGAs, firmware and/or program logic which in combination with the computer system causes or programs the computer system 600 to be a special-purpose machine. According to one embodiment, the techniques herein are performed by the computer system 600 in response to the processor 604 executing one or more sequences of one or more instructions contained in the main memory 606. Such instructions may be read into the main memory 606 from another storage medium, such as the storage device 610. Execution of the sequences of instructions contained in the main memory 606 causes the processor 604 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may include non-volatile media and/or volatile media. Non-volatile media includes, for example, optical or magnetic disks, such as the storage device 610. Volatile media includes dynamic memory, such as the main memory 606. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire, and fiber optics, including the wires that include the bus 602. Transmission media can also take the form of acoustic or light waves, such as those generated during radio-wave and infra-red data communications.

Various forms of media may be involved in carrying one or more sequences of one or more instructions to the processor 604 for execution. For example, the instructions may initially be carried on a magnetic disk or solid state drive of a remote computer. The remote computer can load the instructions into its dynamic memory and send the instructions over a network connection. A modem or network interface local to the computer system 600 can receive the data. The bus 602 carries the data to the main memory 606, from which the processor 604 retrieves and executes the instructions. The instructions received by the main memory 606 may optionally be stored on the storage device 610 either before or after execution by the processor 604.

The computer system 600 also includes a communication interface 618 coupled to the bus 602. The communication interface 618 provides a two-way data communication coupling to a network link 620 that is connected to a local network 622. For example, the communication interface 618 may be an integrated services digital network (ISDN) card, cable modem, satellite modem, or a modem to provide a data communication connection to a corresponding type of telephone line. Wireless links may also be implemented. In any such implementation, the communication interface 618 sends and receives electrical, electromagnetic, or optical signals that carry digital data streams representing various types of information.

The network link 620 typically provides data communication through one or more networks to other data devices. For example, the network link 620 may provide a connection through the local network 622 to a host computer 624 or to data equipment operated by an Internet Service Provider (ISP) 626. The ISP 626 in turn provides data communication services through the worldwide packet data communication network now commonly referred to as the "Internet" 628. The local network 622 and Internet 628 both use electrical, electromagnetic, or optical signals that carry digital data streams. The signals through the various networks and the signals on the network link 620 and through the communication interface 618, which carry the digital data to and from the computer system 600, are example forms of transmission media.

The computer system 600 can send messages and receive data, including program code, through the network(s), the network link 620, and communication interface 618. In the Internet example, a server 630 might transmit a requested code for an application program through the Internet 628, ISP 626, local network 622, and communication interface 618. The received code may be executed by the processor 604 as it is received, and/or stored in the storage device 610, or other non-volatile storage for later execution.

Figure 7:
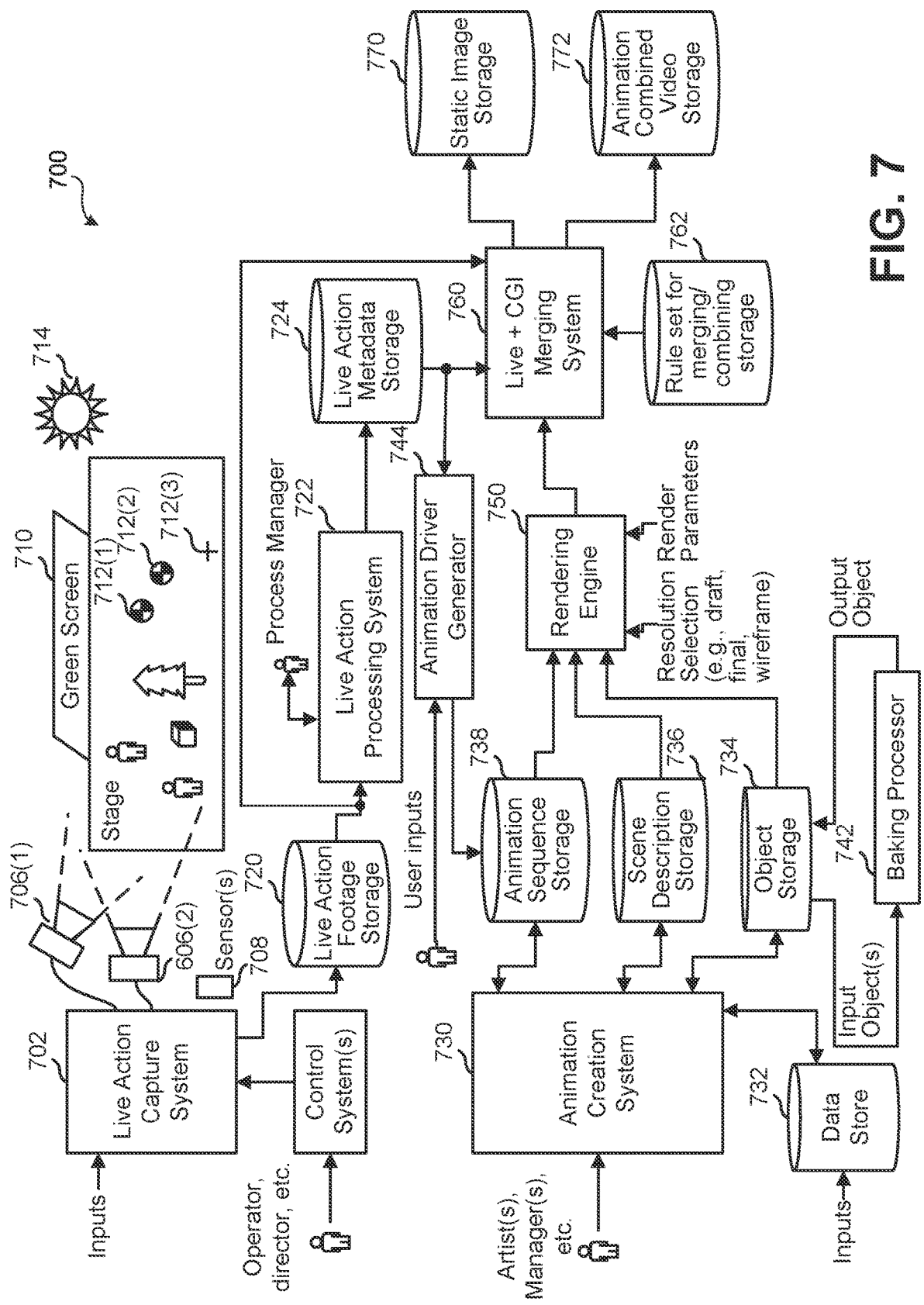
FIG. 7 illustrates an example visual content generation system as might be used to generate imagery in the form of still images and/or video sequences of images.

For example, FIG. 7 illustrates the example visual content generation system 700 as might be used to generate imagery in the form of still images and/or video sequences of images. The visual content generation system 700 might generate imagery of live action scenes, computer generated scenes, or a combination thereof. In a practical system, users are provided with tools that allow them to specify details, such as at high levels and low levels where necessary, what is to go into that imagery. For example, a user may employ the visual content generation system 700 to capture interaction between two human actors performing live on a sound stage and replace one of the human actors with a computer-generated anthropomorphic non-human being that behaves in ways that mimic the replaced human actor's movements and mannerisms, and then add in a third computer-generated character and background scene elements that are computer-generated, all in order to tell a desired story or generate desired imagery.

Still images that are output by the visual content generation system 700 might be represented in computer memory as pixel arrays, such as a two-dimensional array of pixel color values, each associated with a pixel having a position in a two-dimensional image array. Pixel color values might be represented by three or more (or fewer) color values per pixel, such as a red value, a green value, and a blue value (e.g., in RGB format). Dimension of such a two-dimensional array of pixel color values might correspond to a preferred and/or standard display scheme, such as 1920 pixel columns by 1280 pixel rows. Images might or might not be stored in a compressed format, but either way, a desired image may be represented as a two-dimensional array of pixel color values. In another variation, images are represented by a pair of stereo images for three-dimensional presentations and in other variations, some or all of an image output might represent three-dimensional imagery instead of just two-dimensional views.

A stored video sequence might include a plurality of images such as the still images described above, but where each image of the plurality of images has a place in a timing sequence and the stored video sequence is arranged so that when each image is displayed in order, at a time indicated by the timing sequence, the display presents what appears to be moving and/or changing imagery. In one representation, each image of the plurality of images is a video frame having a specified frame number that corresponds to an amount of time that would elapse from when a video sequence begins playing until that specified frame is displayed. A frame rate might be used to describe how many frames of the stored video sequence are displayed per unit time. Example video sequences might include 24 frames per second (24 FPS), 50 FPS, 140 FPS, or other frame rates. In some embodiments, frames are interlaced or otherwise presented for display, but for the purpose of clarity of description, in some examples, it is assumed that a video frame has one specified display time and it should be understood that other variations are possible.

One method of creating a video sequence is to simply use a video camera to record a live action scene, i.e., events that physically occur and can be recorded by a video camera. The events being recorded can be events to be interpreted as viewed (such as seeing two human actors talk to each other) and/or can include events to be interpreted differently due to clever camera operations (such as moving actors about a stage to make one appear larger than the other despite the actors actually being of similar build, or using miniature objects with other miniature objects so as to be interpreted as a scene containing life-sized objects).

Creating video sequences for story-telling or other purposes often calls for scenes that cannot be created with live actors, such as a talking tree, an anthropomorphic object, space battles, and the like. Such video sequences might be generated computationally rather than capturing light from live scenes. In some instances, an entirety of a video sequence might be generated computationally, as in the case of a computer-animated feature film. In some video sequences, it is desirable to have some computer-generated imagery and some live action, perhaps with some careful merging of the two.

While computer-generated imagery might be creatable by manually specifying each color value for each pixel in each frame, this is likely too tedious to be practical. As a result, a creator uses various tools to specify the imagery at a higher level. As an example, an artist might specify the positions in a scene space, such as a three-dimensional coordinate system, of objects and/or lighting, as well as a camera viewpoint, and a camera view plane. Taking all of that as inputs, a rendering engine may compute each of the pixel values in each of the frames. In another example, an artist specifies position and movement of an articulated object having some specified texture rather than specifying the color of each pixel representing that articulated object in each frame.

In a specific example, a rendering engine performs ray tracing wherein a pixel color value is determined by computing which objects lie along a ray traced in the scene space from the camera viewpoint through a point or portion of the camera view plane that corresponds to that pixel. For example, a camera view plane might be represented as a rectangle having a position in the scene space that is divided into a grid corresponding to the pixels of the ultimate image to be generated, and if a ray defined by the camera viewpoint in the scene space and a given pixel in that grid first intersects a solid, opaque, blue object, that given pixel is assigned the color blue. Of course, for modern computer-generated imagery, determining pixel colors—and thereby generating imagery—can be more complicated, as there are lighting issues, reflections, interpolations, and other considerations.

As illustrated in FIG. 7, a live action capture system 702 captures a live scene that plays out on a stage 704. The live action capture system 702 is described herein in greater detail, but might include computer processing capabilities, image processing capabilities, one or more processors, program code storage for storing program instructions executable by the one or more processors, as well as user input devices and user output devices, not all of which are shown.

In a specific live action capture system, cameras 706(1) and 706(2) capture the scene, while in some systems, there might be other sensor(s) 708 that capture information from the live scene (e.g., infrared cameras, infrared sensors, motion capture ("mo-cap") detectors, etc.). On the stage 704, there might be human actors, animal actors, inanimate objects, background objects, and possibly an object such as a green screen 710 that is designed to be captured in a live scene recording in such a way that it is easily overlaid with computer-generated imagery. The stage 704 might also contain objects that serve as fiducials, such as fiducials 712(1)-(3) that might be used post-capture to determine where an object was during capture. A live action scene might be illuminated by one or more lights, such as an overhead light 714.

During or following the capture of a live action scene, the live action capture system 702 might output live action footage to a live action footage storage 720. A live action processing system 722 might process live action footage to generate data about that live action footage and store that data into a live action metadata storage 724. The live action processing system 722 might include computer processing capabilities, image processing capabilities, one or more processors, program code storage for storing program instructions executable by the one or more processors, as well as user input devices and user output devices, not all of which are shown. The live action processing system 722 might process live action footage to determine boundaries of objects in a frame or multiple frames, determine locations of objects in a live action scene, where a camera was relative to some action, distances between moving objects and fiducials, etc. Where elements are sensed or detected, the metadata might include location, color, and intensity of the overhead light 714, as that might be useful in post-processing to match computer-generated lighting on objects that are computer-generated and overlaid on the live action footage. The live action processing system 722 might operate autonomously, perhaps based on predetermined program instructions, to generate and output the live action metadata upon receiving and inputting the live action footage. The live action footage can be camera-captured data as well as data from other sensors.

An animation creation system 730 is another part of the visual content generation system 700. The animation creation system 730 might include computer processing capabilities, image processing capabilities, one or more processors, program code storage for storing program instructions executable by the one or more processors, as well as user input devices and user output devices, not all of which are shown. The animation creation system 730 might be used by animation artists, managers, and others to specify details, perhaps programmatically and/or interactively, of imagery to be generated. From user input and data from a database or other data source, indicated as a data store 732, the animation creation system 730 might generate and output data representing objects (e.g., a horse, a human, a ball, a teapot, a cloud, a light source, a texture, etc.) to an object storage 734, generate and output data representing a scene into a scene description storage 736, and/or generate and output data representing animation sequences to an animation sequence storage 738.

Scene data might indicate locations of objects and other visual elements, values of their parameters, lighting, camera location, camera view plane, and other details that a rendering engine 750 might use to render CGI imagery. For example, scene data might include the locations of several articulated characters, background objects, lighting, etc. specified in a two-dimensional space, three-dimensional space, or other dimensional space (such as a 2.5-dimensional space, three-quarter dimensions, pseudo-3D spaces, etc.) along with locations of a camera viewpoint and view place from which to render imagery. For example, scene data might indicate that there is to be a red, fuzzy, talking dog in the right half of a video and a stationary tree in the left half of the video, all illuminated by a bright point light source that is above and behind the camera viewpoint. In some cases, the camera viewpoint is not explicit, but can be determined from a viewing frustum. In the case of imagery that is to be rendered to a rectangular view, the frustum would be a truncated pyramid. Other shapes for a rendered view are possible and the camera view plane could be different for different shapes.

The animation creation system 730 might be interactive, allowing a user to read in animation sequences, scene descriptions, object details, etc. and edit those, possibly returning them to storage to update or replace existing data.

As an example, an operator might read in objects from object storage into a baking processor that would transform those objects into simpler forms and return those to the object storage 734 as new or different objects. For example, an operator might read in an object that has dozens of specified parameters (movable joints, color options, textures, etc.), select some values for those parameters and then save a baked object that is a simplified object with now fixed values for those parameters.

Rather than have to specify each detail of a scene, data from the data store 732 might be used to drive object presentation. For example, if an artist is creating an animation of a spaceship passing over the surface of the Earth, instead of manually drawing or specifying a coastline, the artist might specify that the animation creation system 730 is to read data from the data store 732 in a file containing coordinates of Earth coastlines and generate background elements of a scene using that coastline data.

Animation sequence data might be in the form of time series of data for control points of an object that has attributes that are controllable. For example, an object might be a humanoid character with limbs and joints that are movable in manners similar to typical human movements. An artist can specify an animation sequence at a high level, such as "the left hand moves from location (X1, Y1, Z1) to (X2, Y2, Z2) over time T1 to T2", at a lower level (e.g., "move the elbow joint 2.5 degrees per frame") or even at a very high level (e.g., "character A should move, consistent with the laws of physics that are given for this scene, from point P1 to point P2 along a specified path").

Animation sequences in an animated scene might be specified by what happens in a live action scene. An animation driver generator 744 might read in live action metadata, such as data representing movements and positions of body parts of a live actor during a live action scene, and generate corresponding animation parameters to be stored in the animation sequence storage 738 for use in animating a CGI object. This can be useful where a live action scene of a human actor is captured while wearing mo-cap fiducials (e.g., high-contrast markers outside actor clothing, high-visibility paint on actor skin, face, etc.) and the movement of those fiducials is determined by the live action processing system 722. The animation driver generator 744 might convert that movement data into specifications of how joints of an articulated CGI character are to move over time.

A rendering engine 750 can read in animation sequences, scene descriptions, and object details, as well as rendering engine control inputs, such as a resolution selection and a set of rendering parameters. Resolution selection might be useful for an operator to control a trade-off between speed of rendering and clarity of detail, as speed might be more important than clarity for a movie maker to test a particular interaction or direction, while clarity might be more important that speed for a movie maker to generate data that will be used for final prints of feature films to be distributed. The rendering engine 750 might include computer processing capabilities, image processing capabilities, one or more processors, program code storage for storing program instructions executable by the one or more processors, as well as user input devices and user output devices, not all of which are shown.

The visual content generation system 700 can also include a merging system 760 that merges live footage with animated content. The live footage might be obtained and input by reading from the live action footage storage 720 to obtain live action footage, by reading from the live action metadata storage 724 to obtain details such as presumed segmentation in captured images segmenting objects in a live action scene from their background (perhaps aided by the fact that the green screen 710 was part of the live action scene), and by obtaining CGI imagery from the rendering engine 750.

A merging system 760 might also read data from a rulesets for merging/combining storage 762. A very simple example of a rule in a ruleset might be "obtain a full image including a two-dimensional pixel array from live footage, obtain a full image including a two-dimensional pixel array from the rendering engine 750, and output an image where each pixel is a corresponding pixel from the rendering engine 750 when the corresponding pixel in the live footage is a specific color of green, otherwise output a pixel value from the corresponding pixel in the live footage."

The merging system 760 might include computer processing capabilities, image processing capabilities, one or more processors, program code storage for storing program instructions executable by the one or more processors, as well as user input devices and user output devices, not all of which are shown. The merging system 760 might operate autonomously, following programming instructions, or might have a user interface or programmatic interface over which an operator can control a merging process. In some embodiments, an operator can specify parameter values to use in a merging process and/or might specify specific tweaks to be made to an output of the merging system 760, such as modifying boundaries of segmented objects, inserting blurs to smooth out imperfections, or adding other effects. Based on its inputs, the merging system 760 can output an image to be stored in a static image storage 770 and/or a sequence of images in the form of video to be stored in an animated/combined video storage 772.

Thus, as described, the visual content generation system 700 can be used to generate video that combines live action with computer-generated animation using various components and tools, some of which are described in more detail herein. While the visual content generation system 700 might be useful for such combinations, with suitable settings, it can be used for outputting entirely live action footage or entirely CGI sequences. The code may also be provided and/or carried by a transitory computer readable medium, e.g., a transmission medium such as in the form of a signal transmitted over a network.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

Although the description has been described with respect to particular embodiments thereof, these particular embodiments are merely illustrative, and not restrictive. For example, in some implementations, a plurality of image capture devices may be used to capture images from various angles of the same live action scene or to capture different portions of the live action scene and the images may be stitched together or particular images selected for the output image. In various implementations, additional equipment, techniques, and technologies may be employed to accommodate requirements of a particular visual production and live action scene, such as underwater scenes.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nano-engineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above. A computer readable medium can comprise any medium for carrying instructions for execution by a computer, and includes a tangible computer readable storage medium and a transmission medium, such as a signal transmitted over a network such as a computer network, an optical signal, an acoustic signal, or an electromagnetic signal.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A method for detecting one or more active marker units in performance capture associated with a virtual production, the method comprising:
   providing the one or more active marker units attached to an object in a live action scene, each of the one or more active marker units being configured to emanate at least one wavelength of electromagnetic radiation in response to signals from a signal controller;
   detecting by a plurality of sensor devices, a presence of electromagnetic radiation captured in frames produced by the plurality of sensor devices;
   generating marker data associated with the detected presence of electromagnetic radiation; and
   determining according to the marker data, by the one or more processors, that the frames represent at least one active marker unit of the one or more active marker units, based, at least in part, on the frames corresponding with predefined frames associated with blocks of time expected to include the at least one wavelength of electromagnetic radiation emanating from the at least one active marker unit.

2. The method of claim 1, wherein the one or more active marker units include a first active marker unit that emanates a first wavelength of electromagnetic radiation and a second active marker unit that emanates a second wavelength of electromagnetic radiation that is different from the first wavelength of electromagnetic radiation.

3. The method of claim 1, wherein the at least one active marker unit emanates a first wavelength of electromagnetic radiation at a first time period and emanates a second wavelength of electromagnetic radiation at a second time period.

4. The method of claim 3, wherein emanating of the first wavelength of electromagnetic radiation is in response to first signals from the signal controller and emanating of the second wavelength of electromagnetic radiation is in response to second signals from the signal controller.

5. The method of claim 4, further comprising:
   determining target marker parameters suitable for a current condition, wherein the first signals and second signals are responsive to the target marker parameters.

6. The method of claim 1, wherein the one or more active marker units simultaneously emanate a first wavelength of electromagnetic radiation and a second wavelength of electromagnetic radiation.

7. The method of claim 6, wherein a first portion of a diffuser of the at least one active marker unit is transmissive to the first wavelength of electromagnetic radiation and a second portion of the diffuser is transmissive for the second wavelength of electromagnetic radiation.

8. The method of claim 1, wherein determining that the frames represent the at least one active marker unit is further based on verification that the at least one wavelength of electromagnetic radiation is captured by at least two sensor devices of the plurality of sensor devices during the blocks of time.

9. A non-transitory computer-readable storage medium carrying program instructions thereon to detect one or more active marker units in attached to an object in a live action scene of a virtual production, the instructions when executed by one or more processors cause the one or more processors to perform operations comprising:
generating marker data associated with a presence of at least one wavelength of electromagnetic radiation captured in frames produced by a plurality of sensor devices, the at least one wavelength of electromagnetic radiation emanated from the one or more active marker units in response to signals received from a signal controller; and
determining according to the marker data that the frames represent at least one active marker unit of the one or more active marker units, based, at least in part, on the frames corresponding with predefined frames associated with blocks of time expected to include the at least one wavelength of electromagnetic radiation emanating from the at least one active marker unit.

10. The computer-readable storage medium of claim 9, wherein the at least one active marker unit emanates a first wavelength of electromagnetic radiation at a first time period and emanates a second wavelength of electromagnetic radiation at a second time period.

11. The computer-readable storage medium of claim 10, wherein emanating of the first wavelength of electromagnetic radiation is in response to first signals from the signal controller and emanating of the second wavelength of electromagnetic radiation is in response to second signals from the signal controller.

12. The computer-readable storage medium of claim 11, the operations further comprise:
determining target marker parameters suitable for a current condition, wherein the first signals and second signals are responsive to the target marker parameters.

13. The computer-readable storage medium of claim 9, wherein the one or more active marker units simultaneously emanate a first wavelength of electromagnetic radiation and a second wavelength of electromagnetic radiation.

14. The computer-readable storage medium of claim 9, wherein determining that the frames represent the at least one active marker unit is further based on verification that the at least one wavelength of electromagnetic radiation is captured by at least two sensor devices of the plurality of sensor devices during the blocks of time.

15. A system to detect an active marker unit in performance capture associated with a virtual production, the system comprising:
one or more active marker units attached to an object in a live action scene, each of the one or more active marker units being configured to emanate at least one wavelength of electromagnetic radiation in response to signals received from a signal controller;
a plurality of sensor devices configured to capture a presence of electromagnetic radiation in frames; and
a computer device comprising:
one or more processors; and
one or more non-transitory computer-readable media with logic encoded thereon, the one or more processors executing the logic to perform operations comprising:
generating marker data associated with the presence of electromagnetic radiation captured in the frames; and
determining according to the marker data that the frames represent at least one active marker unit of the one or more active marker units, based, at least in part, on the frames corresponding with predefined frames associated with blocks of time expected to include the at least one wavelength of electromagnetic radiation emanating from the one or more active marker units.

16. The system of claim 15, wherein the at least one active marker unit includes a first active marker unit that emanates a first wavelength of electromagnetic radiation and a second active marker unit that emanates a second wavelength of electromagnetic radiation that is different from the first wavelength of electromagnetic radiation.

17. The system of claim 15, wherein the at least one active marker unit emanates a first wavelength of electromagnetic radiation at a first time period and emanates a second wavelength of electromagnetic radiation at a second time period.

18. The system of claim 15, wherein the one or more active marker units simultaneously emanate a first wavelength of electromagnetic radiation and a second wavelength of electromagnetic radiation.

19. The system of claim 18, wherein a first portion of a diffuser of the at least one active marker unit is transmissive to the first wavelength of electromagnetic radiation and a second portion of the diffuser is transmissive for the second wavelength of electromagnetic radiation.

20. The system of claim 15, wherein determining that the frames represent the at least one active marker unit is further based on verification that the at least one wavelength of electromagnetic radiation is captured by at least two sensor devices of the plurality of sensor devices during the blocks of time.

* * * * *